United States Patent [19]

Wannlund

[11] Patent Number: 5,188,965
[45] Date of Patent: Feb. 23, 1993

[54] REAGENT SOURCE FOR CHEMILUMINESCENT REACTIONS, TEST KIT, AND METHOD FOR USE

[75] Inventor: Jon C. Wannlund, San Diego, Calif.

[73] Assignee: Difco Laboratories, Detroit, Mich.

[21] Appl. No.: 867,280

[22] Filed: Apr. 9, 1992

Related U.S. Application Data

[63] Continuation of Ser. No. 672,042, Mar. 18, 1991, abandoned.

[51] Int. Cl.⁵ .................... G01N 21/03; G01N 21/75
[52] U.S. Cl. .................................. 436/165; 436/166
[58] Field of Search ............................ 436/165, 166

[56] References Cited

U.S. PATENT DOCUMENTS

| 4,511,533 | 4/1985 | Guadagno et al. | 422/61 |
|---|---|---|---|
| 4,770,856 | 9/1988 | Uthemann et al. | 422/104 |
| 4,902,629 | 2/1990 | Meserol et al. | 436/165 |
| 4,985,631 | 1/1991 | Wannlund et al. | 250/361 R |

OTHER PUBLICATIONS

A Lundin et al., "Bacteriuria Testing by the ATP Method as an Integral Part in the Diagnosis and Therapy of Urinary Tract Infection (UTI)", J. Bioluminescence and Chemiluminescence, vol. 4, pp. 381–389 (1989).

N. Yu. Filippova et al., "New Approaches to the Preparation and Application of Firefly Luciferase", J. Bioluminescence and Chemiluminescence, vol. 4, pp. 419–422 (1989).

A. Roda et al., "Coupled Reactions for the Determination of Analytes and Enzymes Based on the Use of Luminescence", J. Bioluminescence and Chemiluminescence, vol. 4, pp. 423–435 (1989).

Loic J. Blum et al., "Design of Luminescence Photobiosensors", J. Bioluminescence and Chemiluminescence, vol. 4, pp. 543–550 (1989).

Stefano Girotti et al., "Methodological Problems of Direct Bioluminescent ATP Assay in Platelets and Erythrocytes", J. Bioluminescence and Chemiluminescence, vol. 4, pp. 594–601 (1989).

*Primary Examiner*—John W. Rollins
*Attorney, Agent, or Firm*—Gregory Garmong

[57] ABSTRACT

At least some of the reagents required for a chemiluminescent reaction are dried on a piece of a carrier material. The reagents are stable for extended periods of time, without refrigeration, in this form. The sheet of carrier material is of a shape and size to fit flat against the interior surface of a transparent wall of a test well through which light output of the reaction is measured. Light output is thereby concentrated in a region adjacent the wall, minimizing attenuation of the light in passing from the well to permit measurement of low light output levels.

19 Claims, 2 Drawing Sheets

REAGENT SOURCE FOR CHEMILUMINESCENT REACTIONS, TEST KIT, AND METHOD FOR USE

This application is a continuation of application Ser. No. 07/672042, filed Mar. 18, 1991 now abandoned.

BACKGROUND OF THE INVENTION

This invention relates to the utilization of chemiluminescent reactions, and, more particularly, to the presentation format for reactants useful in chemiluminescent reactions.

In several types of chemical and medical test procedures, a liquid such as a food product or a body fluid must be reacted with individual reactants in a sequence of related but separate chemical reactions, and then the final product analyzed. Traditionally, such procedures have been performed by placing the fluid into a reaction tube or the like, adding the remaining reactants for the first reaction, and permitting the first reaction to proceed to completion. The further reactants for the second reaction are added, and the second reaction is permitted to proceed to completion. This stepwise operation can be repeated as many times as necessary, until a final reaction product is obtained for analysis. This technique is not particularly suitable for conducting measurements of reaction such as those that produce measurable light by chemiluminescence, because of the time required to conduct the final mixing and place the reaction tube into a light-measurement apparatus.

In an alternative approach better suited for the measurement of chemiluminescent reactions, a plastic test plate having multichambered test wells has been developed. A liquid test sample is placed into a sample receiving chamber, which has a sloping wall, and mixed with reactants previously placed into the first chamber. The test plate is tilted so that the mixture flows along the sloping wall of the sample receiving chamber and into a reaction measurement chamber. The reaction measurement chamber is preferably cylindrical in shape with a flat bottom that is pressed against a piece of photographic film. The mixture from the sample receiving chamber mixes with additional reactants and the light-producing reaction occurs if the original test sample contained a chemical under test. The intensity of any resulting light is measured through the transparent flat bottom of the reaction measurement chamber. The apparatus for conducting such testing is disclosed in U.S. Pat. No. 4,985,631.

The light intensity produced by many chemiluminescent reactions of interest is quite low, and a continuing problem has been the most efficient utilization of the light produced in the test well. Very sensitive (fast) film can be used to record the light. A number of light intensifying techniques have been used. Various geometries of the test well have been tried, in an effort to concentrate the light onto the film.

A related problem is the stability of the reagents stored in the well. In one highly sensitive form of chemiluminescence, luciferin and luciferase are reacted together with adenosine triphosphate (ATP) to produce light. The ATP is normally provided from the test specimen by a chemical release sequence that is operable only to release ATP under carefully selected circumstances. The luciferin and luciferase are provided in the test well, and there react with the ATP, if any, released from the test sample.

The chemiluminescent reagent luciferase has a relatively short period of full activity after preparation. After a few hours, the activity or reactive strength of the luciferase begins to deteriorate. The result of this deterioration is that the maximum light output of the chemiluminescent reaction, once it occurs, also is less than for freshly prepared luciferase. With prolonged storage, the luciferase becomes so weak that the light output is insufficient for exposure of the film, and the testing procedure becomes inoperable. Luciferase can be stored at reduced temperatures to prolong its active life, but for many applications such as remote sites or clinics, reduced temperature storage is not feasible or inconvenient.

Thus, the viability of chemiluminescent testing often can be linked to the potential light intensity of the reaction, and thence to the loss of that potential as a result of deterioration during storage of the reagents. There is a continuing need for improved techniques for improving the light intensity of the reaction, and retaining that maximum intensity even with prolonged storage of the reagents. The present invention fulfills this need, and further provides related advantages.

SUMMARY OF THE INVENTION

The present invention provides a reagent delivery format that enhances light output intensity for both freshly prepared and stored reagents, and simultaneously improves the storability of the reagents without the need for refrigeration. The approach is fully compatible with the use of a test plate with test wells, and is inexpensive to use. The delivery format also is simple for untrained persons to use, and is quite tidy.

In accordance with the invention, a reagent source for use in a test wherein chemiluminescent light output is measured from a test well having a transparent wall of a preselected peripheral shape and size through which the light output is measured, comprises a sheet of solid carrier material having a portion of the reactants required for a chemiluminescent chemical reaction contained therein in a solid form. Preferably, the sheet has a size and shape such that it fits flat against an interior surface of a transparent wall of a test well having a selected peripheral shape and size through which the light output is measured.

Such a sheet of solid carrier material can be used in a test kit for measuring reactions. In accordance with this embodiment of the invention, a test kit for use in measurements of chemiluminescent light output comprises a test well having a transparent wall with an interior surface, and a sheet of solid carrier material having a portion of the reactants required for a chemiluminescent chemical reaction contained therein in a solid form, the sheet having a size and shape such that it fits against the interior surface of the transparent wall of the test well.

Further in accordance with the invention, a process for performing a test for the presence of a reactant in a sample fluid comprises the steps of furnishing a test well having a transparent wall of a selected peripheral shape and size, and furnishing a sheet of solid carrier material having a portion of the reactants required for a chemiluminescent chemical reaction contained therein in a solid form, the sheet having a size and shape such that it fits flat against the interior surface of the transparent wall of the test well. A sample fluid that may contain a portion of the reactants required for the chemiluminescent chemical reaction is added to the test well, the test well and the sample fluid together containing all of the reactants required for the chemiluminescent chemical reaction in the event of a positively testing sample but not containing all of the reactants required for the chemiluminescent chemical reaction in the event of a negatively testing sample. The light output of the chemiluminescent chemical reaction, if any, is measured through the transparent wall of the test well.

The chemiluminescent test reaction typically requires at least two independent stages of reaction, such as the release of the ATP from the test sample and subsequently the reaction of the released ATP with luciferin and luciferase to produce light which is emitted from the test well and measured. Luciferase is inherently unstable in its freshly prepared liquid form.

In the present approach, the luciferase and preferably also the luciferin are absorbed into a piece of the carrier material. The chemiluminescent activity of the luciferase has been found to be significantly stabilized in this solid form. It can enter into reactions and produce a high intensity of light output following a much longer period of ambient temperature storage than possible for conventional luciferase.

The placing of the luciferin and luciferase onto the carrier material permits them to be located in close proximity to the inside surface of the transparent wall of the test well. One of the major sources of loss of intensity of the emitted light from chemiluminescent reactions in prior approaches has been the attenuation of the light as it passes through the liquid reaction medium, which may be cloudy, opaque, or otherwise not fully transparent. When the luciferin and luciferase are provided in solution, as is normally the case, the chemiluminescent light is necessarily produced throughout a volume, and some light intensity is lost by this liquid volume attenuation effect. Even where the luciferin and luciferase are freeze dried to the inside of the transparent surface, they dissolve into the liquid sample and diffuse into the volume of the liquid so that the reacted light output is attenuated if the fluid is not highly transparent.

In the present approach, the luciferin and luciferase are maintained in close proximity to the transparent wall through which the light is measured, excluding most of the liquid sample material that would otherwise attenuate the light output. The luciferin and luciferase are bound to the carrier material and do not desorb into the liquid sample in the time required for the chemiluminescent reaction to occur. The light source that is measured is therefore pressed tightly against the transparent wall or window through which intensity is measured. Carefully controlled tests have demonstrated that the intensity of light reaching the photographic film may be as much as 50 (or more) times greater where the luciferin and luciferase are bound to a carrier material pressed against the transparent wall, than where they are dissolved throughout the volume of liquid.

The reagents are readily dried onto the appropriately sized sheets of a carrier material such as paper. Alternatively, they may be absorbed onto large sheets and then individually sized pieces cut therefrom.

In an extension of the above-described approach, multiple paper layers can be stacked in the bottom of the reaction well. For example, the reagents required for the light-producing reaction are contained within a first carrier sheet, as just described. The reagents required for the ATP-release reaction are contained within a second carrier sheet, using a similar approach. The bottom side of the first carrier sheet is pressed tightly against the transparent wall. Then the second carrier sheet is pressed against the top side of the first carrier sheet. When a test sample is added to the test well, it first encounters the second carrier sheet, resulting in the release of ATP. The liquid sample with the released ATP diffuses (soaks) through the second carrier sheet and into the first carrier sheet, where the released ATP reacts with the luciferin and luciferase to produce light that is measured through the transparent wall of the test well. In this manner a single chamber in the well can function to permit multiple sequential reactions to be conductd and the resulting light output measured. This approach is somewhat less quantitative than the multi-chamber technique, but is operable for qualitative and semi-quantitative studies in many cases.

The present invention provides an important advance in increasing the measurable light output of chemiluminescent reactions conducted in test wells, both without and with extended storage. Other features and advantages of the invention will be apparent from the following more detailed description of the preferred embodiment, taken in conjunction with the accompanying drawings, which illustrate, by way of example, the principles of the invention.

DETAILED DESCRIPTION OF THE PREFERRED EMBODIMENTS

Figure 1:
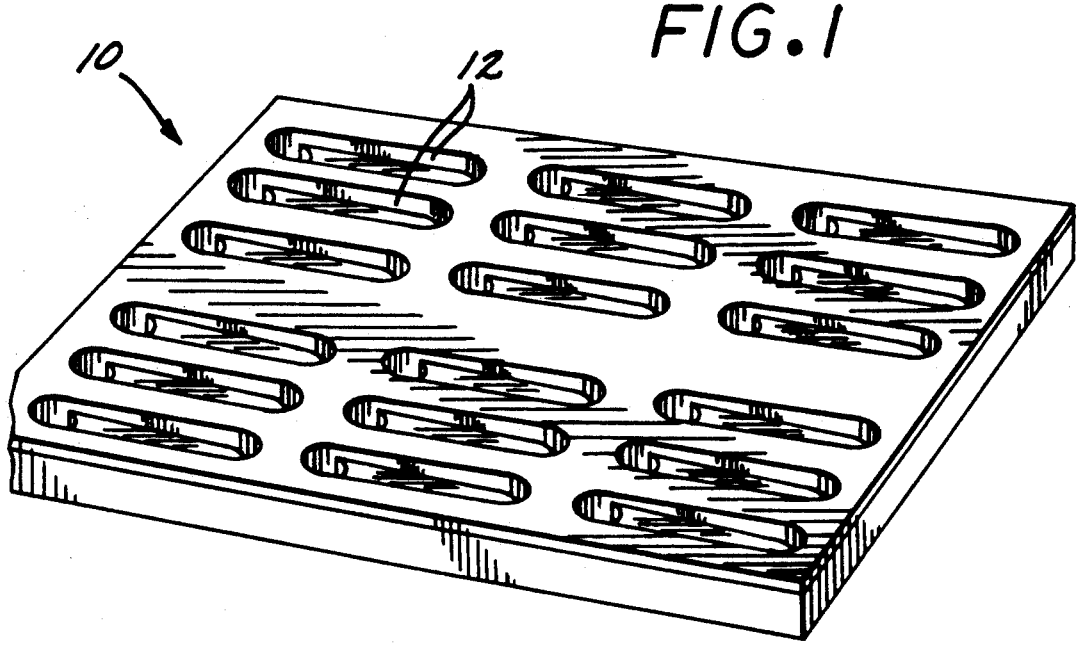
FIG. 1 is a perspective view of a test plate.
Figure 2:
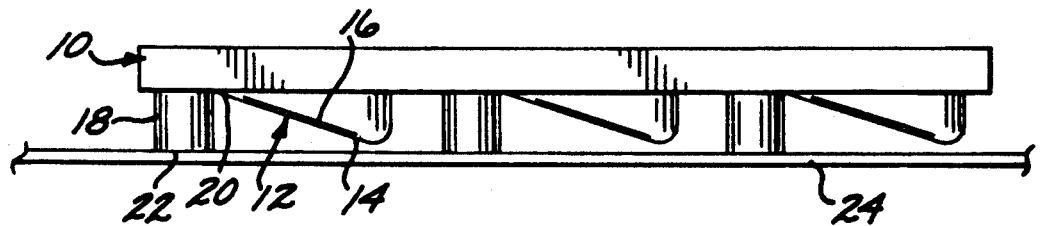
FIG. 2 is a side elevational view of the test plate of FIG. 1.

FIGS. 1 and 2 illustrate a test plate 10 having a plurality of test wells 12 therein. The presently preferred use of the invention is in conjunction with such as test plate 10, although it is not so limited. The present invention is widely applicable to other uses of chemiluminescent reaction chemistry.

Each test well 12 includes a sample receiving chamber 14 extending downwardly from the test plate 10. The sample receiving chamber 14 has on one side an upwardly sloping interior wall 16 that slopes upwardly and outwardly from the bottom of the chamber 14. A reaction measurement chamber 18 is positioned adjacent the sample receiving chamber 14, near a top end 20 of the upwardly sloping interior wall 16. The reaction measurement chamber 18 is illustrated as a generally cylindrical cup with an open top and a transparent, closed, flat bottom 22.

In the use of the test plate 10 according to one approach, an aqueous liquid specimen such as urine or other fluid being tested for the presence of bacteria is placed into the sample receiving chamber 14 and reacted with a first reactant previously placed into the chamber 14. When sufficient time has passed for the first reaction to be as complete as required, one end of the test plate 10 (in the illustration of FIG. 2 the right end) is displaced upwardly so that the test plate 10 is rotated (counterclockwise in FIG. 2). The reacted liquid speciment in the sample receiving chamber 14 flows along the sloping interior wall 16 and thence into the reaction measurement chamber 18, where it reacts with a second reactant. Light produced by the chemical reaction is recorded on a piece of light-sensitive photographic film 24 against which the bottom 22 of the reaction measurement chamber 18 is pressed.

In one preferred application of the test plate 10, the present invention is used for analysis of the bacteria content of urine samples, food samples, or other liquids. This test depends upon the reaction of bacterial adenosine triphosphate (ATP) with luminescent reagents, to produce light that is measured through the bottom 22 of the test well 12. There are two sources of ATP in a urine sample, bacterial and non-bacterial sources. The objective of the bacteriuria test is to measure bacterial sources only. In the test, the ATP in non-bacterial sources is first removed so that it cannot adversely affect the test results, and then the ATP in bacterial sources is released and reacted with the luminescent reagents.

In this test procedure, the sample receiving chamber 14 contains a release reactant to lyse somatic cells, releasing non-bacterial ATP therefrom. The release reactant does not affect the bacterial ATP, which remains within the bacteria. The release reactant is Triton ® ×100 detergent (polyoxyethylene ether). The sample receiving chamber 14 also contains an enzyme, ATP elimination reactant (preferably apyrase) to dephosphorolate the non-bacterial ATP to adenosene monophosphate, also known as AMP, which is not measured by the subsequent luminescent assay. The preferred elimination reactant is apyrase enzyme.

To prepare the reagent used in the sample receiving chamber 14, about 0.16 units of solid apyrase enzyme and about 100 microliters of 0.2 percent aqueous solution of Triton ×100 detergent liquid are mixed with 0.5 milligrams of bovine serum albumin. This mixture is added to the sample receiving chamber 14 and freeze dried.

In the reaction measurement chamber 18, the bacterial ATP is released, and reacted with luminescent reagents. The result is light produced in proportion to the bacterial ATP, with the amount of light measured indicating the amount of bacterial ATP present in the specimen. In the prior approach, which is useful in many cases and is described in U.S. Pat. No. 4,985,631, whose disclosure is incorporated by reference, to prepare the solid material for the reaction measurement chamber 18, the following ingredients are mixed together: about 100 microliters of a 0.005 percent to 0.6 percent concentration aqueous solution of a chemical bacterial releasing agent (such as polyoxyethylene ether, hexachlorophene, chlorohexadine, or dimethylsulfoxide), about 10 to 100 micrograms of firefly luciferase enzyme, about 15 micrograms of solid D-luciferin, about 10 microliters of a 10 millimolar magnesium chloride luminescent cofactor, about 0.5 milligrams of bovine serum albumin, and a N-2-Hydroxyethylpiperadine- N'-2-ethanesulfonic acid buffer to bring the pH of the solution to 7.75. The solution is added to the reaction measurement chamber 18 and freeze dried.

Figure 3:
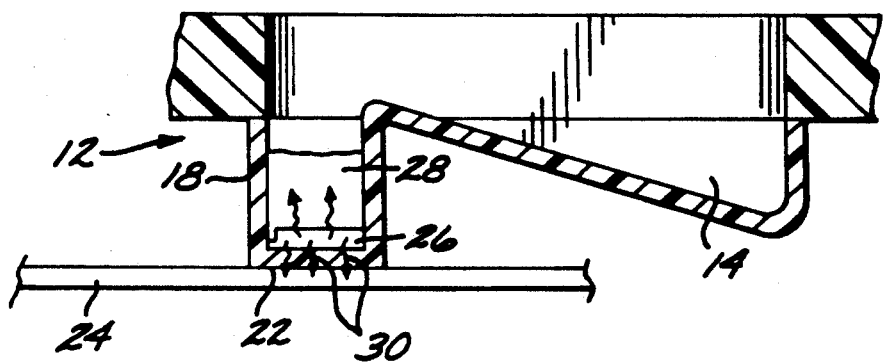
FIG. 3 is an enlarged fragmented sectional view of one of the test wells of FIG. 2, where chemiluminescent reagents are provided on a sheet of carrier material.

The approach of the present invention is illustrated in FIG. 3, showing one of the test wells of FIG. 2 in greater detail. The ATP release reagents added to the sample receiving chamber 14 are as described previously. The chemiluminescent reagents are provided to the reaction measurement chamber 18 absorbed into a sheet of carrier material 26. These reagents are prepared as just described, and then blotted into properly sized pieces of paper, the preferred carrier material 26. Most preferably, the amount of liquid reagent is about two milligrams per square millimeter of paper, this concentration controlling the light output intensity.

The pieces of carrier material 26 are cut or punched to a shape that is substantially the same as the inside of the reaction measurement chamber 18 at its bottom 22. The size of the pieces of carrier material 26 is preferably about the same as the size of the chamber 18 at its bottom. This size for the carrier material 26 permits it to be forced flat against the interior surface of the transparent wall, in this case the bottom 22 of the chamber 18, and then held in place by friction or a restraining member as will be described subsequently. The piece of carrier material 26 does not move or shift about, even when the test plate 10 is inverted. By way of example and not of limitation, in a preferred approach the interior of the reaction measurement chamber 18 is a cylinder, with an inside diameter at the bottom 22 of about 5.8 millimeters. The piece of carrier material 26 is a round disk of paper into which about 15 microliters of luciferase/-luciferin reagent has been soaked and dried. The diameter of the disk is from about 2.5 to about 6 millimeters, with the most preferred diameter being about 5 millimeters. Alternatively, an adhesive could be used to hold the piece of carrier material 26 in place, but that has not been found necessary.

Figure 4:
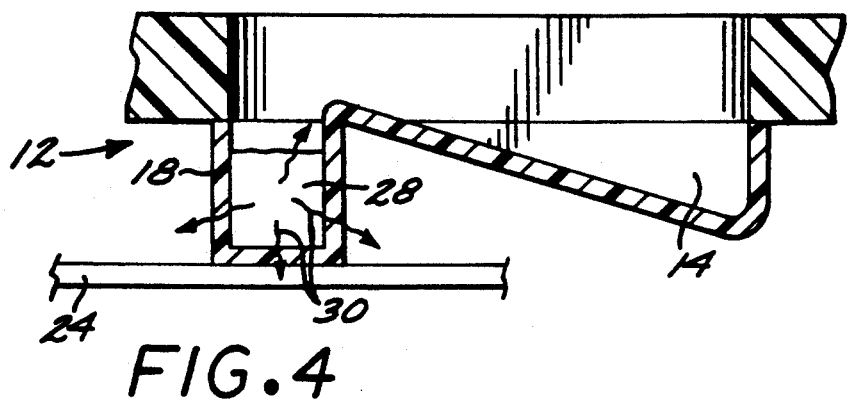
FIG. 4 is an enlarged fragmented sectional view like that of FIG. 3, except where a chemiluminescent reaction occurs throughout the volume of the reaction measurement chamber.

A comparison of the light paths for the present approach of FIG. 3 and the prior approach of FIG. 4 illustrates one reason for the improved light intensity reaching the film 24 achieved in the present approach. A fluid sample 28 is illustrated in each of the reaction measurement chambers 18 of FIGS. 3 and 4. In the prior approach of FIG. 4, the luciferase and luciferin are mixed throughout the volume of the fluid sample 28, and light rays produced by the chemiluminescent reaction must travel varying path lengths 30 to reach the film 24. In some cases the light paths 30 are long, leading to a high degree of light attenuation by the fluid sample itself. By contrast, in the approach of the present invention shown in FIG. 3, the light paths 30 to the film are all short, because the luciferin and luciferase are retained within the carrier material 26, which is pressed against the inside of the bottom window 22 just a short distance from the film 24. There is less attenuation of the light beams 30 in the present approach of FIG. 3 than the prior approach of FIG. 4, because the light path 30 does not extend through any significant amount of sample material in the approach of FIG. 3. If the fluid sample 28 is cloudy or opaque, the attenuation becomes such a significant factor that the prior approach of FIG. 4 may be inoperable, while the present approach of FIG. 3 remains fully operable.

As will be illustrated in the examples that follow, the absorption and drying of the luciferase/luciferin reagent for the reaction measurement chamber 18 also prolongs the active life and activity of this reagent. The pieces of carrier material may be stored in inert atmosphere for extended periods of time without substantial loss of activity of the reagent. The result is that the maximum possible activity of the reagents provided in the form of carrier materials with absorbed reagent is greater than the liquid reagent stored for the same period of time.

The following examples illustrate aspects of the invention, and should not be taken as limiting of the invention in any respect.

EXAMPLE 1

Test wells were prepared using the present approach of FIG. 3 (with the reagents used in the reaction measurement chamber 18 absorbed into a paper carrier material and dried) and the prior approach of FIG. 4 (using liquid reagents). Portions of the same ATP concentration were tested in each approach about 1 hour after the luciferin/luciferase reagent was prepared, with all testing parameters the same. The recorded light output for the present approach was about 1168 relative light units, while the recorded light output for the prior approach was about 26 relative light units.

The present approach provides improved light output for freshly prepared reagents.

EXAMPLE 2

Example 1 was repeated, except that the comparative testing was conducted 22 days after the preparation of the reagents. The conventionally furnished luciferin/luciferase liquid reagent was stored at a refrigerated temperature of 4° C., while the carrier material with luciferin/luciferase reagent were stored at ambient temperature. The measured light output was 2 relative light units for the conventional approach, and 1156 relative light units for the present approach.

The present approach provides a substantially improved light intensity after storage of the reagents in solid form in the carrier material, as compared with the use of stored liquid reagents. The light intensity of the present approach with stored reagent was not significantly less than for freshly prepared reagent.

EXAMPLE 3

Example 1 was repeated using samples of chocolate milk shake for analysis. This sample material has been intentionally contaminated with bacteria to produce the same ATP concentration as in Example 1. The measured light output was 0 for the conventional approach, and 1148 relative light units for the present approach. The output for the conventional approach was so low that the testing procedure was inoperable, as a result of the test sample being opaque. Even though light was presumably produced from the chemiluminescent reaction in the conventional approach, it could not reach the recording film.

Figure 5:
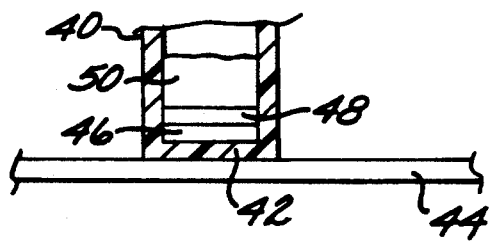
FIG. 5 is an enlarged fragmented sectional view of a single-chamber test well using multiple carrier sheets for multiple reactants.
Figure 6:
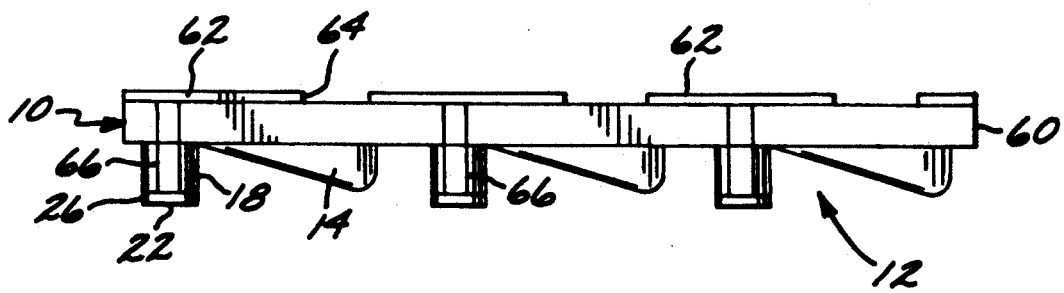
FIG. 6 is a side view like that of FIG. 2, of another embodiment.

Another application of the carrier material approach of the present invention is illustrated in FIG. 5. A single chamber well 40 has a flat, transparent bottom 42 contacting a piece of film 44. A first piece of carrier material 46 is pressed flat against the inside of the bottom 42 of the well 40. This piece 46 has the luciferin/luciferase reagent contained therein. A second piece of carrier material 48 is pressed flat against the top of the first piece 46. The second piece of carrier material has the ATP release reagent contained therein. Both the luciferin/luciferase reagent and the ATP reagent are prepared as described previously. A drop of the luciferin/luciferase reagent is placed onto the first piece of carrier material 46, and a drop of the ATP release reagent is placed onto the second piece of carrier material 48. The drops are allowed to dry in a heated air stream. The two pieces of carrier material 46 and 48 are pushed to the bottom of the well 40, the first piece of carrier material being pushed into the well first so that it directly contacts the inside surface of the bottom 42.

A fluid sample 50 is placed into the well 40. Sample material percolates downwardly through the second piece of carrier material 46, with the ATP release reaction occurring simultaneously so that released ATP is produced. The liquid with released ATP continues to percolate downwardly into the first piece of carrier material 46, where the released ATP reacts with the luciferin/luciferase reagent therein to produce light that is recorded on the film 44.

This single-chamber approach has the advantage of simplicity, because only a single well is required and the reagent carrier pieces can be loaded into the well at the factory. There is minimal chance of erroneous results resulting from mistakes by the technician performing the test. However, the results are not as consistent and quantitative as with the two-chamber approach because of the possible variations in percolation rate through the carrier pieces 46 and 48. Thus, the approach of FIG. 5 is more simply performed but less quantitative than that of FIGS. 1-3. The approach of FIG. 5 may be of most value in rough screening procedures performed at clinics or in self-testing, while that of FIGS. 1-3 is more quantitative.

EXAMPLE 4

A single-chamber test apparatus like that of FIG. 5 was prepared using the approach just described. A bacterially contaminated sample was placed into the test well, and the light produced by the chemiluminescent reaction successfully recorded.

In a particularly preferred embodiment of the invention, the small sheet or disk of carrier material 26 may be physically restrained in place in the bottom of the reaction measurement chamber 18 to prevent it from floating in the liquid sample and to prevent air bubbles from being captured between the carrier material 26 and the bottom 22 of the chamber 18. In one approach, a cover sheet 62 of paper with adhesive on its bottom side (or, equivalently, strips of tape) is fixed to the top of a body 60 of the test plate 10 in which the test wells 12 are supported. The cover sheet 62 has die cut openings 64 therethrough (equivalently, spaces are left between strips of tape, if used) at locations just above the sample receiving chambers 14, so that liquid samples can be metered into the receiving chambers 14. The cover sheet 62 provides a place for identification information to be written above each test well 14 as it is used.

Before the adhesive paper sheet 62 is fixed in place on the top of the body 60 of the test plate 10, the carrier material 26 is placed into each reaction measurement chamber 18, and a length of restraining member 66 is placed upright in each of the reaction measurement chambers 18 on top of the carrier material 26. A convenient and inexpensive restraining member 66 is a length of hollow plastic soda straw. The length of the restraining member 66 is sufficiently long that it just reaches to the top of the body 60 to contact the underside of the adhesive paper sheet 62, or may be very slightly longer. Thus, when the adhesive paper sheet 62 is fixed in place on the top of the body 60, it contacts the restraining member 66 to prevent it from moving. The restraining member 66 in turn contacts the carrier material 26 and prevents it from moving during transport of the test plate 10, and also from floating or otherwise moving when the reaction measurement chamber 18 is filled with a liquid sample during testing. Such a test kit is physically robust and resistant to loss of effectiveness due to jarring or shaking prior to use. It is also resistant to loss of effectiveness due to floating of the carrier material during testing procedures or entrapment of air bubbles between the carrier material and the bottom of the reaction measurement chamber.

The present approach provides an important advance in the art of chemiluminescent testing procedures. Light intensity is increased for both unstored and stored reagents. Although a particular embodiment of the invention has been described in detail for purposes of illustration, various modifications may be made without departing from the spirit and scope of the invention. Accordingly, the invention is not to be limited except as by the appended claims.

What is claimed is:

1. A reagent source for use in a test wherein chemiluminescent light output is measured from a test well having a transparent wall of a preselected peripheral shape and size through which the light output is measured, comprising:
   a sheet of solid carrier material having a portion of the reactants required for a chemiluminescent chemical reaction contained therein in a solid form.

2. The reagent source of claim 1, wherein the sheet has a size and shape such that it fits flat against an interior surface of a transparent wall of a test well having a preselected peripheral shape and size through which the light output is measured.

3. The reagent source of claim 1, wherein the carrier material is paper.

4. The reagent source of claim 1, wherein the reactant contained within the carrier material includes luciferase.

5. The reagent source of claim 1, wherein the reactant contained within the carrier material includes luciferin.

6. The reagent source of claim 1, wherein the sheet of solid carrier material is round with a diameter of about 5 millimeters.

7. The reagent source of claim 1, further including a second sheet of solid carrier material having at least one of the reactants required for a chemiluminescent chemical reaction contained therein in a solid form.

8. A test kit for use in measurements of chemiluminescent light output, comprising:
   a test well having a transparent wall with an interior surface; and
   a sheet of solid carrier material having a portion of the reactants required for a chemiluminescent chemical reaction contained therein in a solid form, the sheet having a size and shape such that it fits against the interior surface of the transparent wall of the test well.

9. The test kit of claim 8, wherein the test well is supported in a test plate.

10. The test kit of claim 8, wherein the carrier material is paper.

11. The test kit of claim 8, wherein the reactant contained within the carrier material includes luciferase.

12. The test kit of claim 8, wherein the reactant contained within the carrier material includes luciferin.

13. The test kit of claim 8, further including
    means for restraining the sheet of solid carrier material from movement away from the interior surface of the transparent wall of the test well.

14. The test kit of claim 13, wherein the means for restraining includes
    a cover sheet fixed to the surface of the test plate, and
    a length of a restraining member captured between the cover sheet and the sheet of carrier material.

15. The test kit of claim 9, further including a plurality of test wells supported in the test plate.

16. A process for performing a test for the presence of a reactant in a sample fluid, comprising the steps of:
    furnishing a test well having a transparent wall of a preselected peripheral shape and size;
    furnishing a sheet of solid carrier material having a portion of the reactants required for a chemiluminescent chemical reaction contained therein in a solid form, the sheet having a size and shape such that it fits flat against an interior surface of the transparent wall of the test well;
    adding to the test well a sample fluid that may contain a portion of the reactants required for the chemiluminescent chemical reaction, the test well and the sample fluid together containing all of the reactants required for the chemiluminescent chemical reaction in the event of a positively testing sample but not containing all of the reactants required for the chemiluminescent chemical reaction in the event of a negatively testing sample; and
    measuring the light output of the chemiluminescent chemical reaction, if any, through the transparent wall of the test well.

17. The process of claim 16, wherein the step of furnishing a sheet of solid carrier material includes the steps of:
    preparing a liquid solution of the portion of the reactants in a liquid carrier,
    applying a quantity of the liquid solution to a piece of untreated carrier material to permit the liquid solution to soak into the carrier material, and
    evaporating the liquid carrier to leave the portion of reactants in the carrier material.

18. The process of claim 16, wherein the sample fluid is at least partially opaque to visible light.

19. The process of claim 16, wherein the carrier material is paper.

* * * * *